(12) United States Patent
Scivoletto

(10) Patent No.: US 11,602,541 B2
(45) Date of Patent: Mar. 14, 2023

(54) NASAL SPRAY COMPOSITION

(71) Applicant: Joseph Scivoletto, Margate, FL (US)

(72) Inventor: Joseph Scivoletto, Margate, FL (US)

( * ) Notice: Subject to any disclaimer, the term of this patent is extended or adjusted under 35 U.S.C. 154(b) by 0 days.

(21) Appl. No.: 17/237,497

(22) Filed: Apr. 22, 2021

(65) Prior Publication Data

US 2021/0330704 A1 Oct. 28, 2021

Related U.S. Application Data

(60) Provisional application No. 63/015,155, filed on Apr. 24, 2020.

(51) Int. Cl.
*A61K 33/06* (2006.01)
*A61K 45/06* (2006.01)
*A61K 31/4406* (2006.01)

(52) U.S. Cl.
CPC .......... *A61K 33/06* (2013.01); *A61K 31/4406* (2013.01); *A61K 45/06* (2013.01)

(58) Field of Classification Search
None
See application file for complete search history.

(56) References Cited

U.S. PATENT DOCUMENTS

| | | |
|---|---|---|
| 6,929,800 B2 * | 8/2005 | Salman .................. A61K 33/32 424/641 |
| 7,862,808 B2 | 1/2011 | Isolauri et al. |
| 9,011,941 B2 | 4/2015 | Jones et al. |
| 9,694,042 B1 | 7/2017 | Terry et al. |
| 10,376,548 B2 * | 8/2019 | Scivoletto .............. A23K 20/24 |
| 2004/0062801 A1 | 4/2004 | Faour et al. |
| 2005/0031708 A1 | 2/2005 | Portney |
| 2007/0148187 A1 | 6/2007 | Scivoletto |
| 2014/0228304 A1 | 8/2014 | Jones et al. |
| 2018/0200189 A1 | 7/2018 | Vetter |

OTHER PUBLICATIONS

Davani-Davari et al., Foods (2019), 8(3), pp. 1/27-27/27.*

* cited by examiner

*Primary Examiner* — Brian J Davis
(74) *Attorney, Agent, or Firm* — Johnson & Martin, P.A.; James David Johnson

(57) ABSTRACT

Compositions and methods for treating and preventing respiratory symptoms related to viral and bacterial infections are described. The composition includes water, ionic minerals, trace minerals, a niacin-related compound, and an optional ingredient. The optional ingredient is mastic gum, a prebiotic, or both. The niacin-related compound is methyl nicotinate, nicotinic acid, nicotinamide, niacin, or a combination of two or more of the foregoing. The method involves nasal, auricular, or oral administration or a combination of two or more of the foregoing routes of administration to a human or other mammal.

18 Claims, No Drawings

NASAL SPRAY COMPOSITION

CROSS-REFERENCE TO RELATED APPLICATIONS

This application is a nonprovisional application of and claims priority from U.S. provisional patent application Ser. No. 63/015,155 filed on Apr. 24, 2020. The foregoing application is incorporated in their entirety herein by reference.

FIELD OF THE INVENTION

The invention relates to compositions and methods used as medical treatments. More particularly, the invention related to compositions and methods for treating and preventing symptoms related to viral and bacterial infections of a respiratory system and ears of a human or other mammal.

BACKGROUND

The human nose is more than just a flap of flesh and cartilage on the front of the face. Besides being part of the respiratory system that inhales oxygen and exhales carbon dioxide, the nose also contributes to other important functions, such as hearing and tasting. Human noses can have a wide array of shapes and sizes due to genetics and injuries. The two openings in the nose care called nostrils, or napes. They lead to two nasal cavities that are separated by the septum, which is a wall of cartilage. Inside the face is an intricate system of canals and pockets of air called sinus cavities. Sinus cavities span all the way to the back of the skull, right above the oral cavity, within the cheekbones, and between the eyes and brows. All of these areas are responsible, at least in part, for breathing, smelling, tasting, and immune system defense. The human nose can smell over one trillion scents, according to researchers. The nose smells with the olfactory cleft, which is the roof of the nasal cavity next to the "smelling" part of the brain, which consists of the olfactory bulb and fossa. This part of the nose has many nerve endings that carry smell sensations to the brain via the nasal passageways on either side of the nose, which open into the choana and then into a chamber called the nasopharynx, which is the upper part of the throat. This chamber opens into the oropharynx, the throat area behind the mouth. When air is inhaled through the nostrils, it travels through the nasal passages, the choana, the nasopharynx, the oropharynx, and the voice box and ends up in the lungs. In the respiratory system, the nose is a passageway for air.

Part of the function of the nose is to provide pre-warming and humidification of inhaled air as well as some heat recovery and moisture recovery of air exhaled from the lungs. In addition, particulate filtering and smelling of the air is also performed by the nose with the sense of smell also contributing to the sense of taste. The nose also contributes to speech faculty. The mucous secreting membrane together with the cilia perform a filtering function and a mucosal-ciliary transport system for the filtered material. The amount of mucous being secreted in 24 hours can be up to one liter. Mucous membranes of the nasal cavity and paranasal sinuses can more than double their secretion when inflamed or stimulated. The mucous is also one of the first lines of immune defense due to the presence of immunoglobulins within the mucous. The blood supply, local membrane responses, autonomic nerves, and the central nervous system contribute to the level of control of mucous secretion and swelling of the nasal membranes. Furthermore, the membranes of the nose and paranasal sinuses are highly vascular such that compounds absorbed by the membranes can be readily transported to the body by the circulatory system. This cell membrane is made up of lipids that create a barrier to the outside environment that only certain substances can cross to reach the cell interior.

Electricity is everywhere, even in the human body. Our cells are specialized to conduct electrical currents. Electricity is required for the nervous system to send signals throughout the body and to the brain, making it possible for us to move, think and feel. So, how do cells control electrical currents?

The contents of the cell are protected from the outside environment by a cell membrane. This cell membrane is made up of lipids that create a barrier that only certain substances can cross to reach the cell interior. Not only does the cell membrane function as a barrier to molecules, it also acts as a way for the cell to generate electrical currents. Resting cells are negatively charged on the inside while the outside environment is more positively charged, which is due to a slight imbalance between positive and negative ions inside and outside the cell. Cells can achieve this charge separation by allowing charged ions to flow in and out through the membrane. The flow of charges across the cell membrane is what generates electrical currents.

Nasal congestion can also be referred to as nasal blockage, nasal obstruction, blocked nose, stuffy nose, or stuffed up nose. Nasal congestion can have many multi-factorial causes and can range from a mild annoyance to a life-threatening condition. For example, nasal congestion can interfere with hearing and consequently delay speech development in young children. In children and adults, nasal congestion can interfere with sleep, contribute to snoring, and is sometimes associated with sleep apnea. In general, nasal congestion, can also cause, or is associated with postnasal drainage, facial pressure and pain, headaches, and chronic or recurrent sinusitis (i.e., a sinus infection). Other associated effects of nasal congestion in a general order of frequency include dripping of mucous membrane secretions down the throat, abnormal taste sensations, feelings of dryness in the upper respiratory tract, drowsiness, nasal irritation, loss of the sense of smell, burning sensations within the nose, and nose bleeds. Co-morbidity conditions are often overlooked, but can contribute significantly to the burden of nasal congestion and allergic rhinitis (AR) for a patient. Examples of co-morbidity conditions reported in a significant number of patients include asthma, nasal polyps (nasal polyposis), and sleep apnea. Nasal congestion in an infant in the first few months of life can interfere with breast feeding and in severe cases can cause life threatening respiratory distress.

Other symptoms of nasal congestion including, for example, post-nasal drip, headache, ear or hearing issues, loss of smell, facial pain, itchy nose, itchy eyes, watering eyes, runny nose, sneezing, and stuffed nose are common and can be difficult to manage.

Histamine is normally released when a human body detects something harmful, such as an infectious pathogen, e.g., a virus or bacteria. Histamine causes blood vessels to expand (vasodilate) and the skin to swell, which helps protect the body. Such chemical releases by the body cause many of the aforementioned symptoms in individuals suffering from colds, flu, or other respiratory infections. Antihistamine sprays can cause a so-called "nasal spray addiction" in some people. This condition often occurs when a person uses the decongestant nasal spray too frequently or for too long, and is rebound congestion or antihistamine intolerance and not a true addiction. With rebound congestion, a person may find that they need to use the spray more frequently over time, often several times a day or more. Each time the individual uses the spray, the blood vessels in the nose narrow (vassal constructor), causing the tissue inside the nose to shrink. After the medicine wears off, the nasal tissue swells again, sometimes swelling even more than before. If the person continues to use the nasal spray, this swelling can become more severe and lead to permanent swelling of the tissue. Long-term use of these sprays can also damage the tissue, causing infection and pain. Symptoms of rebound congestion or dependency on nasal spray may include feeling congested again shortly after using a decongestant spray, using a decongestant spray regularly but feeling that it no longer has any effect, feeling a strong urge to use the spray more often than the instructions recommend, and using the spray just to be able to breathe normally on a daily basis.

To help people avoid this problem, the American Academy of Asthma, Allergy, and Immunology (AAAAI) recommend using nasal sprays no more than twice a day for only three days. Those who have been using a nasal spray more frequently should consult with a doctor who can examine the nasal tissue to check for damage or excess swelling. Typically, a person will need to stop using the spray and may need a different medication to relieve the swelling, such as a steroid nasal spray.

In addition, some people abuse pseudoephedrine by using it to make an illegal recreational drug, methamphetamine, according to information from the American Academy of Family Physicians. For this reason, some states may require a doctor's prescription for these products. In others, pharmacies may keep products containing this chemical behind the counter, even though they do not need a prescription. Some jurisdictions and retailers also impose a limit on the amount of such products an individual can purchase each month, and individuals may have to show identification or give personal details when they buy this type of decongestant.

Food grade methyl nicotinate (MN) is a methyl ester of nicotinic acid (NA). Methyl nicotinate is a rubefacient, which is capable of transdermal penetration to produce vasodilation through the production of prostaglandin D2 (PGD2), which is an indicator of preventing the blood vessels in the nose to narrow and causing the tissue inside the nose to shrink.

Postnasal drip is extra mucus felt in the back of the nose and throat caused by the glands in those areas. Individuals experiencing postnasal drip usually feel they have to clear their throats more than normal. The excess mucus can also cause some other symptoms. The nose, throat, and sinuses are all constantly producing mucus. Mucus is a thick and slippery substance that helps to keep the airways from drying out throughout the day. The air people breathe is full of germs, pollen, and other environmental pollutants. When the air enters the body, these particles can create problems if they are not filtered out before reaching the lungs. Mucus performs an important bodily function by trapping these foreign bodies and helping to eliminate them. Mucus usually goes unnoticed as it harmlessly mixes with saliva throughout the day and is swallowed or blown from the nose. However, if the body produces too much mucus, it becomes much more noticeable. When this happens, a person may feel mucus dripping down the back of their throat. This is what is known as postnasal drip.

In addition to the sensation of mucus dripping down the back of the throat, symptoms of postnasal drip include sore or scratchy throat, feelings of nausea caused by extra mucus in the stomach, frequently clearing the throat, excessive spitting up or swallowing mucus, bad breath, and a cough that worsens at night.

A need exists for compositions and methods for treating and preventing symptoms related to viral and bacterial infections of a respiratory system and ears of a human or other mammal. A need also exists for compositions and methods for treating postnasal drip, nasal congestion, and other cold, flu, and allergy symptoms. A further need exists for compositions and methods for treating and preventing symptoms related to viral and bacterial infections of a respiratory system and ears of a human or other mammal while avoiding the use of anti-histamine sprays. Yet a further need exists for compositions and methods for treating and preventing respiratory symptoms related to pollen, mold, and other allergies of a human or other mammal. Still a further need exists for all-natural, drug-free compositions and methods for treating and preventing respiratory symptoms that affect the nose, nasal passages, ears, sinuses, and upper respiratory system without using chemicals that can be harmful to sensitive cells and tissue and without using pharmaceuticals.

SUMMARY

The invention related to compositions and methods for treating and preventing respiratory symptoms related to viral and bacterial infections. For example, the compositions and methods are useful for treating and preventing conditions of the nasal mucous membrane including over-production of thick nasal mucus. These compositions and methods are useful for treating and preventing cold and flu symptoms such as postnasal drip and nasal congestion. The compositions and methods are also useful for treating other respiratory infection symptoms including symptoms affecting the ears and those related to allergies.

The composition includes water, ionic minerals, trace minerals, a niacin-related compound, and an optional ingredient. The optional ingredient is mastic gum, a prebiotic, or both. The ionic minerals, the trace minerals, the niacin-related compound, mastic gum, and the prebiotic can all be dissolved in water. Thus, some embodiments of the composition include water, ionic minerals, trace minerals, a niacin-related compound, and mastic gum, while other embodiments include water, ionic minerals, trace minerals, a niacin-related compound, and a prebiotic. Still other embodiments include water, ionic minerals, trace minerals, a niacin-related compound, mastic gum, and a prebiotic. The niacin-related compound is methyl nicotinate, nicotinic acid, nicotinamide, niacin, or a combination of two or more of the foregoing. The method involves nasal, auricular, or oral administration or a combination of two or more of the foregoing routes of administration to a human or other mammal.

The ionic minerals and trace minerals of the compositions can be derived from water sourced from a lake or an inland sea such as, for example, the Great Salt Lake, the Dead Sea, or another lake or inland sea. The elements like sodium, potassium, calcium, and magnesium, have a specific electrical charge. Almost all human and mammalian cells can use these negative and positive charged elements, called ions, to generate electricity. Providing these minerals produces healthful effects by improving or facilitating cellular functions including immune system function.

The methods described herein using the composition can treat and prevent nasal congestion, i.e., the blockage of the nasal passages and paranasal sinuses usually from the swelling of membranes lining the nose due to vasodilatation of local blood vessels and/or inflammation of the membranes.

The compositions and methods described herein provide and use novel, formulated compositions for nasal (or auricular or oral) administration to treat and prevent symptoms of a variety of diseases and conditions (including viral and bacterial infections such as, for example, the common cold and influenza) that affect the nasal or paranasal mucous membrane, upper respiratory system, and histamine intolerance. The compositions may also be useful for treatment and reduction of symptoms related to the oral herpes simplex virus. The compositions have antibacterial, antiviral, and antifungal properties.

Several examples of bacterial infections that may be treated or prevented using the compositions and methods described herein have been identified. The compositions may be used to treat *Helicobacter pylori* found in middle ear of children with otitis. The compositions may also be used to treat and kill at least eight oral pathogens such as oral bacteria that cause gum disease. The compositions described herein are more effective at treating and killing such oral bacteria than are the antiseptic agents chlorhexidine digluconate or hydrogen peroxide, but are also less harmful to the cells and tissues of the mouth than are those two antiseptic agents.

The compositions and methods described herein provide advantages in treating and preventing symptoms related to viral and bacterial infections of a respiratory system and ears of a human or other mammal. These compositions and methods also provide advantages in treating postnasal drip, nasal congestion, and other cold, flu, and allergy symptoms. These compositions and methods also provide advantages in treating and preventing symptoms related to viral and bacterial infections of a respiratory system and ears of a human or other mammal while avoiding the use of anti-histamine sprays. These compositions and methods also provide advantages in treating and preventing respiratory symptoms related to pollen, mold, and other allergies of a human or other mammal. These compositions and methods also provide advantages in providing all-natural, drug-free alternatives for treating and preventing respiratory symptoms that affect the nose, nasal passages, ears, sinuses, and upper respiratory system without using chemicals that can be harmful to sensitive cells and tissue and without using pharmaceuticals.

Accordingly, the invention features a composition for treating and preventing respiratory symptoms related to viral and bacterial infections. The composition includes water, ionic minerals, trace minerals, mastic gum, and a niacin-related compound.

In another aspect, the invention can feature the composition further including a prebiotic.

In another aspect, the invention can feature the prebiotic being or including inulin.

In another aspect, the invention can feature the ionic minerals being or including chloride, magnesium, potassium, and sodium.

In another aspect, the invention can feature the trace minerals being or including sulfate, boron, bromide, calcium, carbonate, silicon, nitrogen, selenium, phosphorus, iodine, chromium, iron, manganese, titanium, rubidium, cobalt, copper, antimony, molybdenum, strontium, zinc, nickel, tungsten, germanium, scandium, tin, lanthanum, yttrium, silver, gallium, zirconium, vanadium, beryllium, tellurium, bismuth, hafnium, terbium, europium, gadolinium, samarium, cerium, cesium, gold, dysprosium, or a combination of two or more of the foregoing.

In another aspect, the invention can feature the trace minerals being or including a mixture of minerals derived from saltwater of an inland lake or sea, wherein the mixture includes two or more minerals selected from among the following: sulfate, boron, bromide, calcium, carbonate, silicon, nitrogen, selenium, phosphorus, iodine, chromium, iron, manganese, titanium, rubidium, cobalt, copper, antimony, molybdenum, strontium, zinc, nickel, tungsten, germanium, scandium, tin, lanthanum, yttrium, silver, gallium, zirconium, vanadium, beryllium, tellurium, bismuth, hafnium, terbium, europium, gadolinium, samarium, cerium, cesium, gold, and dysprosium.

In another aspect, the invention can feature the niacin-related compound being or including methyl nicotinate, nicotinic acid, nicotinamide, niacin, or a combination of two or more of the foregoing.

The invention also features a composition for treating and preventing respiratory symptoms related to viral and bacterial infections, wherein the composition includes water, ionic minerals, trace minerals, a prebiotic, and a niacin-related compound.

In another aspect, the invention can feature the composition further including mastic gum.

In another aspect, the invention can feature the ionic minerals being or including chloride, magnesium, potassium, and sodium.

In another aspect, the invention can feature the trace minerals being or including sulfate, boron, bromide, calcium, carbonate, silicon, nitrogen, selenium, phosphorus, iodine, chromium, iron, manganese, titanium, rubidium, cobalt, copper, antimony, molybdenum, strontium, zinc, nickel, tungsten, germanium, scandium, tin, lanthanum, yttrium, silver, gallium, zirconium, vanadium, beryllium, tellurium, bismuth, hafnium, terbium, europium, gadolinium, samarium, cerium, cesium, gold, dysprosium, or a combination of two or more of the foregoing.

In another aspect, the invention can feature the trace minerals including a mixture of minerals derived from saltwater of an inland lake or sea, wherein the mixture includes two or more minerals selected from among the following: sulfate, boron, bromide, calcium, carbonate, silicon, nitrogen, selenium, phosphorus, iodine, chromium, iron, manganese, titanium, rubidium, cobalt, copper, antimony, molybdenum, strontium, zinc, nickel, tungsten, germanium, scandium, tin, lanthanum, yttrium, silver, gallium, zirconium, vanadium, beryllium, tellurium, bismuth, hafnium, terbium, europium, gadolinium, samarium, cerium, cesium, gold, and dysprosium.

In another aspect, the invention can feature the prebiotic being or including inulin.

In another aspect, the invention can feature the niacin-related compound being or including methyl nicotinate, nicotinic acid, nicotinamide, niacin, or a combination of two or more of the foregoing.

A method of the invention can be used for treating and preventing respiratory symptoms related to viral and bacterial infections. The method includes the steps of: (a) providing a composition for treating a human or another mammal having a viral or bacterial infection, the composition including: water, ionic minerals, trace minerals, a niacin-related compound, and an optional ingredient; and (b) administering the composition to the human or other mammal.

Another method of the invention can include step (b) of the method including nasal, auricular, or oral administration or a combination of two or more of the foregoing routes of administration.

Another method of the invention can include the niacin-related compound being or including methyl nicotinate, nicotinic acid, nicotinamide, niacin, or a combination of two or more of the foregoing.

Another method of the invention can include the ionic minerals being or including chloride, magnesium, potassium, and sodium; and the trace minerals being or including sulfate, boron, bromide, calcium, carbonate, silicon, nitrogen, selenium, phosphorus, iodine, chromium, iron, manganese, titanium, rubidium, cobalt, copper, antimony, molybdenum, strontium, zinc, nickel, tungsten, germanium, scandium, tin, lanthanum, yttrium, silver, gallium, zirconium, vanadium, beryllium, tellurium, bismuth, hafnium, terbium, europium, gadolinium, samarium, cerium, cesium, gold, dysprosium, or a combination of two or more of the foregoing.

Another method of the invention can include the optional ingredient being or including mastic gum.

Another method of the invention can include the optional ingredient being or including a prebiotic.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control.

DETAILED DESCRIPTION

The present invention is best understood by reference to the detailed drawings and description set forth herein. Embodiments of the invention are discussed below with reference to the drawings; however, those skilled in the art will readily appreciate that the detailed description given herein with respect to these figures is for explanatory purposes as the invention extends beyond these limited embodiments. For example, in light of the teachings of the present invention, those skilled in the art will recognize a multiplicity of alternate and suitable approaches, depending upon the needs of the particular application, to implement the functionality of any given detail described herein beyond the particular implementation choices in the following embodiments described and shown. That is, numerous modifications and variations of the invention may exist that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The present invention should not be limited to the particular methodology, compounds, materials, manufacturing techniques, uses, and applications, described herein, as these may vary. The terminology used herein is used for the purpose of describing particular embodiments only, and is not intended to limit the scope of the present invention. As used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" may be a reference to one or more steps or means and may include sub-steps and subservient means.

All conjunctions used herein are to be understood in the most inclusive sense possible. Thus, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. Structures described herein are to be understood also to refer to functional equivalents of such structures. Language that may be construed to express approximation should be so understood unless the context clearly dictates otherwise.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," "desirable," or "exemplary" and words of similar meaning should not be understood as implying that certain features are critical, essential, or even important to the structure or function of the invention, but instead as merely intended to highlight alternative or additional features that may or may not be utilized in a particular embodiment of the invention.

Those skilled in the art will also understand that if a specific number of an introduced claim recitation is intended, such an intent will be explicitly recited in the claim, and in the absence of such recitation no such intent is present. For example, as an aid to understanding, the appended claims may contain usage of the introductory phrases "at least one" and "one or more" to introduce claim recitations; however, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C" is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

All numbers expressing dimensions, quantities of ingredients, reaction conditions, and so forth used in the specification are to be understood as being modified in all instances by the term "about" unless expressly stated otherwise. Accordingly, unless indicated to the contrary, the numerical parameters set forth herein are approximations that may vary depending upon the desired properties sought to be obtained.

The invention provides compositions for treating and preventing respiratory symptoms related to viral and bacterial infections are described. For example, the compositions may be used to treat symptoms caused by cold, influenza (flu), and other viral and bacterial infections of the respiratory system, nasal passages, ear, mouth, and throat. The compositions are provided as a liquid and may be delivered as drops or as a spray for nasal, auricular, or oral administration or a combination of two or more of the foregoing routes of administration to a human or other mammal.

The composition includes water, ionic minerals, trace minerals, a niacin-related compound, and an optional ingredient. The optional ingredient is mastic gum, a prebiotic, or both. The niacin-related compound is methyl nicotinate, nicotinic acid, nicotinamide, niacin (also known as vitamin B3), or a combination of two or more of the foregoing. The method involves nasal, auricular, or oral administration or a combination of two or more of the foregoing routes of administration to a human or other mammal.

The ionic minerals, trace minerals, niacin-related compound, mastic gum, and the prebiotic are soluble in water and are dissolved in water to create the composition. The water used to create the various embodiments of the composition can be distilled water or saltwater (i.e., brine). All of the ingredients are dissolved in the water to produce a liquid that can be administered as a spray or as droplets. As a spray, the composition can be administered via nasal, auricular, or oral routes. As liquid drops, the composition can be administered via nasal, auricular, or oral routes. In other embodiments, the composition may be produced as a liquid that is ingestible, for example, as a beverage or as a liquid-form medicine. The composition can be administered using a spray bottle or an atomizer to create a mist for any of the administration routes, using a swab for nasal and auricular administration, or using a dropper for any of the administration routes.

The ionic minerals are included in the compositions to provide anti-inflammatory and anti-oxidant properties. The ionic minerals include one or more of chloride, magnesium, potassium, and sodium; however, in exemplary embodiments, all of the ionic minerals are included.

Like the ionic minerals, the trace minerals are also included in the compositions to provide anti-inflammatory and anti-oxidant properties. The trace minerals include sulfate, boron, bromide, calcium, carbonate, silicon, nitrogen, selenium, phosphorus, iodine, chromium, iron, manganese, titanium, rubidium, cobalt, copper, antimony, molybdenum, strontium, zinc, nickel, tungsten, germanium, scandium, tin, lanthanum, yttrium, silver, gallium, zirconium, vanadium, beryllium, tellurium, bismuth, hafnium, terbium, europium, gadolinium, samarium, cerium, cesium, gold, dysprosium, or a combination of two or more of the foregoing. These trace minerals can be obtained from multiple sources and dissolved in the water of the composition. In other embodiments, the trace minerals are a mixture of minerals derived from saltwater of one or more inland lakes or seas, e.g., the Great Salt Lake or the Dead Sea.

Mastic gum is included in the compositions to provide antiviral, antibacterial, antifungal, anti-inflammatory, and anti-oxidant properties. Mastic gum is made soluble in water using brine or an alcohol.

The niacin-related compound is included in the compositions to cause vasodilation, which prevents the blood vessels in the nose from narrowing and causing the tissue inside the nose to shrink. The niacin-related compound can be methyl nicotinate, nicotinic acid, nicotinamide, niacin, or a combination of two or more of the foregoing. In exemplary embodiments, the niacin-related compound is methyl nicotinate.

The prebiotic is included in the compositions to nourish the growth of beneficial bacteria that exist naturally in the nose, nasal passages, mouth, throat, sinuses, and/or ears. In exemplary embodiments, the prebiotic is inulin. The inulin can be derived from chicory root so that the composition is all-natural. In other embodiments, the prebiotic can be Fibruline® or Fibrulose® chicory root fiber manufactured by Cosucra or Litesse® Powder manufactured by Danisco.

The composition can be made in a number of different embodiments as described below:

Example 1: In one exemplary embodiment, the composition includes water, ionic minerals, trace minerals, a niacin-related compound, mastic gum, and a prebiotic. The ionic minerals include chloride, magnesium, sodium, and potassium. The trace minerals include one or more of the trace minerals described elsewhere herein. The niacin-related compound is methyl nicotinate. In other related embodiments, niacin-related compound can be methyl nicotinate, nicotinic acid, nicotinamide, niacin, or a combination of two or more of the foregoing. The prebiotic can be inulin.

Example 2: In another exemplary embodiment, the composition includes water, ionic minerals, trace minerals, a niacin-related compound, and mastic gum. The ionic minerals include chloride, magnesium, sodium, and potassium. The trace minerals include one or more of the trace minerals described elsewhere herein. The niacin-related compound is methyl nicotinate. In other related embodiments, niacin-related compound can be methyl nicotinate, nicotinic acid, nicotinamide, niacin, or a combination of two or more of the foregoing.

Example 3: In yet another exemplary embodiment, the composition includes water, ionic minerals, trace minerals, a niacin-related compound, and a prebiotic. The ionic minerals include chloride, magnesium, sodium, and potassium. The trace minerals include one or more of the trace minerals described elsewhere herein. The niacin-related compound is methyl nicotinate. In other related embodiments, niacin-related compound can be methyl nicotinate, nicotinic acid, nicotinamide, niacin, or a combination of two or more of the foregoing. The prebiotic can be inulin.

Example 4: In another embodiment, the composition includes only water and mastic gum.

Example 5: In another embodiment, the composition includes water, ionic minerals, trace minerals, and a niacin-related compound. The ionic minerals include chloride, magnesium, sodium, and potassium. The trace minerals include one or more of the trace minerals described elsewhere herein. The niacin-related compound is methyl nicotinate. In other related embodiments, niacin-related compound can be methyl nicotinate, nicotinic acid, nicotinamide, niacin, or a combination of two or more of the foregoing.

Example 6: In another embodiment, the composition includes water, ionic minerals, trace minerals, mastic gum, and a prebiotic. The ionic minerals include chloride, magnesium, sodium, and potassium. The trace minerals include one or more of the trace minerals described elsewhere herein. The prebiotic can be inulin.

Example 7: In another embodiment, the composition includes water, ionic minerals, trace minerals, and mastic gum. The ionic minerals include chloride, magnesium, sodium, and potassium. The trace minerals include one or more of the trace minerals described elsewhere herein.

Example 8: In another embodiment, the composition includes water, ionic minerals, trace minerals, and a prebiotic. The ionic minerals include chloride, magnesium, sodium, and potassium. The trace minerals include one or more of the trace minerals described elsewhere herein. The prebiotic can be inulin.

The ingredients of the composition other than water can be provided in various amounts or percentages by weight. For example, in some embodiments, those ingredients (other than water) are included in the following percentages by weight: about 0.01% to about 82% magnesium, about 0.01% to 25% chloride, less than about 1% to about 10% sodium, less than about 1% to about 10% potassium, about 0.01% to about 10% niacin-related compound, about 0.1% to about 20% mastic gum, and about 0.01% to about 20% prebiotic. In some of these embodiments, the niacin-related compound is methyl nicotinate.

In other embodiments, those ingredients (other than water) are included in the following percentages by weight: about 0.01% to about 82% magnesium, about 0.01% to 25% chloride, less than about 1% to about 10% sodium, less than about 1% to about 10% potassium, about 0.01% to about 10% niacin-related compound, about 0.1% to about 20% mastic gum, and about 0.01% to about 20% prebiotic. In some of these embodiments, the niacin-related compound is methyl nicotinate.

In other embodiments, the composition can include methyl nicotinate at about 0.01% to about 10% by weight with the balance of the composition being water.

In other embodiments, the composition can include methyl nicotinate at about 0.01% to about 10% by weight with the balance of the composition being brine water.

In other embodiments, those ingredients (other than water) are included in the following percentages by weight: about 1% to about 82% magnesium, about 1% to 25% chloride, less than about 1% to about 10% sodium, less than about 1% to about 10% potassium, and about 0.01% to about 10% niacin-related compound. In some of these embodiments, the niacin-related compound is methyl nicotinate. In these embodiments, the water is brine water.

In other embodiments, those ingredients (other than water) are included in the following percentages by weight: about 1% to about 82% magnesium, about 1% to 25% chloride, less than about 1% to about 10% sodium, less than about 1% to about 10% potassium, about 0.01% to about 10% niacin-related compound, and about 1% to about 20% prebiotic. In some of these embodiments, the niacin-related compound is methyl nicotinate.

In still other embodiments, the composition can include methyl nicotinate at about 0.01% to about 10% by weight and mastic gum at about 0.1% to about 20% by weight with the balance of the composition being water.

In yet other embodiments, the non-aqueous ingredients of the composition are included in water in the following percentages by weight: about 28% magnesium, about 69% chloride, about 1% sodium, less than about 1% potassium, about 0.01% to about 10% niacin-related compound, about 0.1% to about 20% mastic gum, and about 0.1% to about 20% prebiotic. In some of these embodiments, the niacin-related compound is methyl nicotinate.

The compositions used herein are used to treat a variety of diseases, conditions, and symptoms of humans and other mammals including, for example, viral infections (such as the common cold, influenza, herpes simplex virus type 2 (HSV-2), coxsackievirus type B3, and adenovirus type 5), bacterial infections (such as *Helicobacter pylori*), fungal infections, and allergies. In connection with the respiratory system, nose, and nasal passages, the compositions can be used to treat and/or to prevent conditions of the nasal or paranasal mucous membrane such as nasal congestion, upper respiratory symptoms, sinusitis (i.e., sinus infections), allergic rhinitis, sinus congestion and pressure, headaches, migraines, vertigo, itchy irritated nasal passages, and post-nasal drip. The compositions and methods are useful for decongesting nasal, sinus, and respiratory openings and passages, shrinking swollen nasal membranes, reducing or eliminating nose and sinus congestion and itchy irritated nasal passages, and for shortening the symptomatic period and/or infectious period of common cold and flu viruses, and for reducing or eliminating negative effects caused by nasal exposure to pollutants, dust, and other airborne contaminants.

In connection with the human ear or ears or the ear or ears of another mammal, the compositions used herein are useful for treating and preventing ear congestion and pressure and for clearing both ear and sinus canals. The compositions assist in clearing mucus where germs and viruses can grow. The compositions also combat sinus and nose congestion, itchy nose, sneezing, runny nose, nose and nasal passage dryness, throat dryness, and snoring. The compositions also alleviate sinus congestion and blocked ears caused by altitude.

Methods of the invention relate to providing a composition selected from among the various compositions, formulations, and embodiments described herein, and administering such composition via nasal, auricular, or oral routes of administration using methods and tools described elsewhere herein (e.g., using a spray bottle, an atomizer, a dropper, etc.).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nasally administrable composition for treating and preventing respiratory symptoms related to viral and bacterial infections, the composition comprising:
    water;
    ionic minerals consisting of chloride, magnesium, potassium, and sodium;
    trace minerals;
    mastic gum; and
    a niacin-related compound comprising methyl nicotinate, nicotinamide, or a combination thereof.

2. The composition of claim 1, further comprising a prebiotic.

3. The composition of claim 2, wherein the prebiotic comprises inulin.

4. The composition of claim 1, wherein the trace minerals comprise at least one trace mineral selected from the group consisting of: sulfate, boron, bromide, calcium, carbonate, silicon, selenium, phosphorus, iodine, chromium, iron, manganese, titanium, rubidium, cobalt, copper, antimony, molybdenum, strontium, zinc, nickel, tungsten, germanium, scandium, tin, lanthanum, yttrium, silver, gallium, zirconium, vanadium, beryllium, tellurium, bismuth, hafnium, terbium, europium, gadolinium, samarium, cerium, cesium, gold, and dysprosium.

5. The composition of claim 1, wherein the trace minerals comprise a mixture of minerals derived from saltwater of an inland lake or sea, wherein the mixture comprises two or more minerals selected from the group consisting of: sulfate, boron, bromide, calcium, carbonate, silicon, selenium, phosphorus, iodine, chromium, iron, manganese, titanium, rubidium, cobalt, copper, antimony, molybdenum, strontium, zinc, nickel, tungsten, germanium, scandium, tin, lanthanum, yttrium, silver, gallium, zirconium, vanadium, beryllium, tellurium, bismuth, hafnium, terbium, europium, gadolinium, samarium, cerium, cesium, gold, and dysprosium.

6. The composition of claim 1, further comprising niacin.

7. A nasally administrable composition for treating and preventing respiratory symptoms related to viral and bacterial infections, the composition comprising:
water;
ionic minerals consisting of chloride, magnesium, potassium, and sodium;
trace minerals; and
mastic gum.

8. The composition of claim 1, wherein the composition comprises a sprayable composition.

9. The composition of claim 1, wherein the composition comprises a sprayable composition that is also auricularly and orally administrable.

10. The composition of claim 1, wherein the composition comprises droplets that are nasally administrable.

11. The composition of claim 1, wherein the composition comprises droplets that are also auricularly and orally administrable.

12. The composition of claim 7, wherein the composition comprises a sprayable composition.

13. The composition of claim 7, wherein the composition comprises a sprayable composition that is also auricularly and orally administrable.

14. The composition of claim 7, further comprising methyl nicotinate.

15. The composition of claim 7, further comprising nicotinamide.

16. The composition of claim 7, further comprising methyl nicotinate and niacin.

17. The composition of claim 7, further comprising nicotinamide and niacin.

18. A nasally administrable composition for treating and preventing respiratory symptoms related to viral and bacterial infections, the composition consisting of:
water;
ionic minerals consisting of chloride, magnesium, potassium, and sodium;
trace minerals;
mastic gum; and
a niacin-related compound consisting of methyl nicotinate, nicotinamide, or a combination thereof.

* * * * *